United States Patent [19]

Lewyn et al.

[11] 4,114,627
[45] Sep. 19, 1978

[54] CARDIAC PACER SYSTEM AND METHOD WITH CAPTURE VERIFICATION SIGNAL

[75] Inventors: Lanny Louis Lewyn, Laguna Beach; Glen David Simpson, Huntington Beach, both of Calif.

[73] Assignee: American Hospital Supply Corporation, Evanston, Ill.

[21] Appl. No.: 750,574

[22] Filed: Dec. 14, 1976

[51] Int. Cl.$^2$ ............................................... H01N 1/36
[52] U.S. Cl. .............................................. 128/419 PT
[58] Field of Search .................. 128/419 PG, 419 PT, 128/419 PS, 419 R, 421, 422, 423, 2.06 B

[56] References Cited

U.S. PATENT DOCUMENTS

| | | | |
|---|---|---|---|
| 3,477,421 | 11/1969 | Partridge | 128/2.06 B |
| 3,498,288 | 3/1970 | Max et al. | 128/2.06 B X |
| 3,593,718 | 7/1971 | Krasner et al. | 128/419 PG |
| 3,648,708 | 3/1972 | Haeri | 128/422 |
| 3,669,120 | 6/1972 | Nielsen | 128/419 PG X |
| 3,769,986 | 11/1973 | Herrmann | 128/421 X |
| 3,830,242 | 8/1974 | Greatbatch | 128/419 PT |
| 3,835,865 | 9/1974 | Bowers | 128/419 PG |
| 3,871,383 | 3/1975 | Lee | 128/419 PS |

FOREIGN PATENT DOCUMENTS 2,520,729  11/1975  Fed. Rep. of Germany .... 128/419 PG

OTHER PUBLICATIONS

Huntsman et al., "IEEE Transactions on Bio-Medical Engineering", vol. 18, No. 4, Jul. 1971, pp. 301+302.

*Primary Examiner*—William E. Kamm
*Attorney, Agent, or Firm*—Emrich, Root, O'Keeffe & Lee

[57] ABSTRACT

A cardiac pacer system includes a pulse generator for generating a stimulating signal coupled through an output coupling capacitor to a single heart-engaging electrode. An amplifier is coupled to the electrode for sensing an R wave. Immediately upon initiation of the stimulating pulse, a discharging resistor for the coupling capacitor is disconnected, and the signal input to the amplifier is uncoupled from the electrode. The amplifier is restrained and its gain is reduced. When the stimulating pulse terminates, the input terminal of the output coupling capacitor is clamped through resistance to ground and discharged rapidly. The current discharging the output coupling capacitor assists in discharging the electrode capacitance. During amplifier restraint, the amplifier input coupling capacitor is allowed to charge to a voltage sufficient to compensate for the voltage offset on the system output coupling capacitor and the electrode capacitance. The output coupling capacitor's discharging current is interrupted when the rate of change of voltage at the output coupling capacitor and electrode will, in a short length of time, reach a value nearly equal to zero; and the voltage offset is compensated. After sensing, the discharging resistor is reconnected, and the gain of the amplifier is returned to its original value.

16 Claims, 7 Drawing Figures

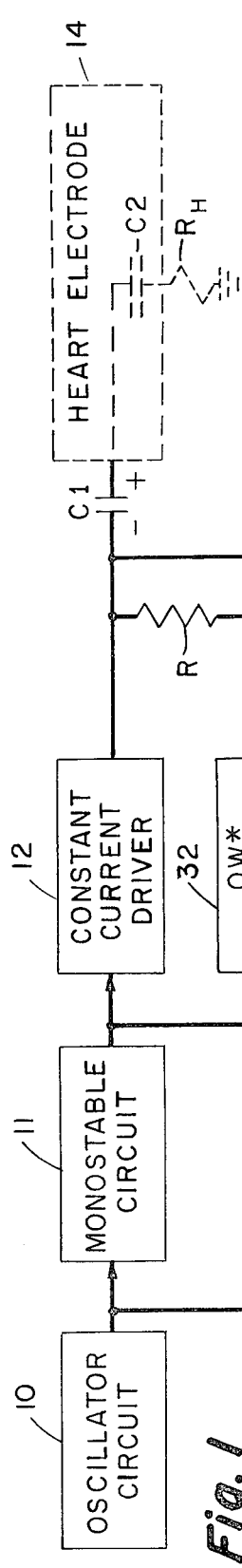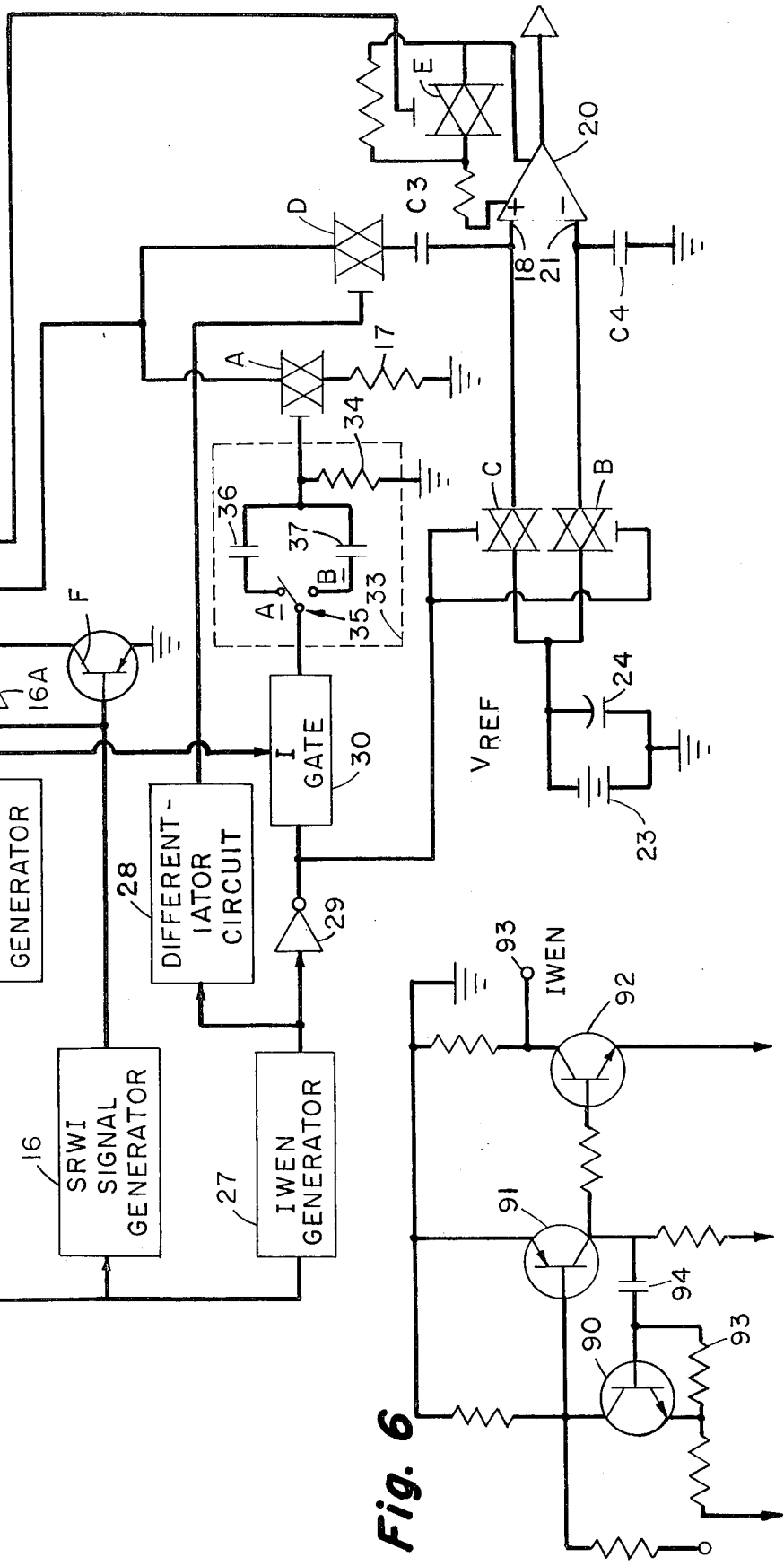

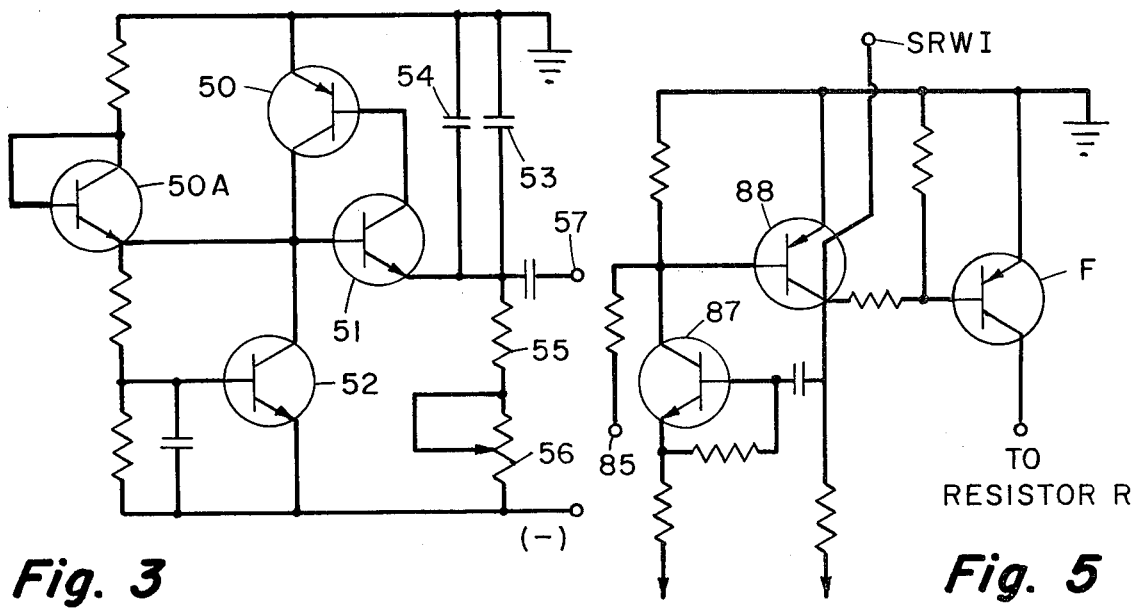
Fig. 3
Fig. 5
Fig. 4
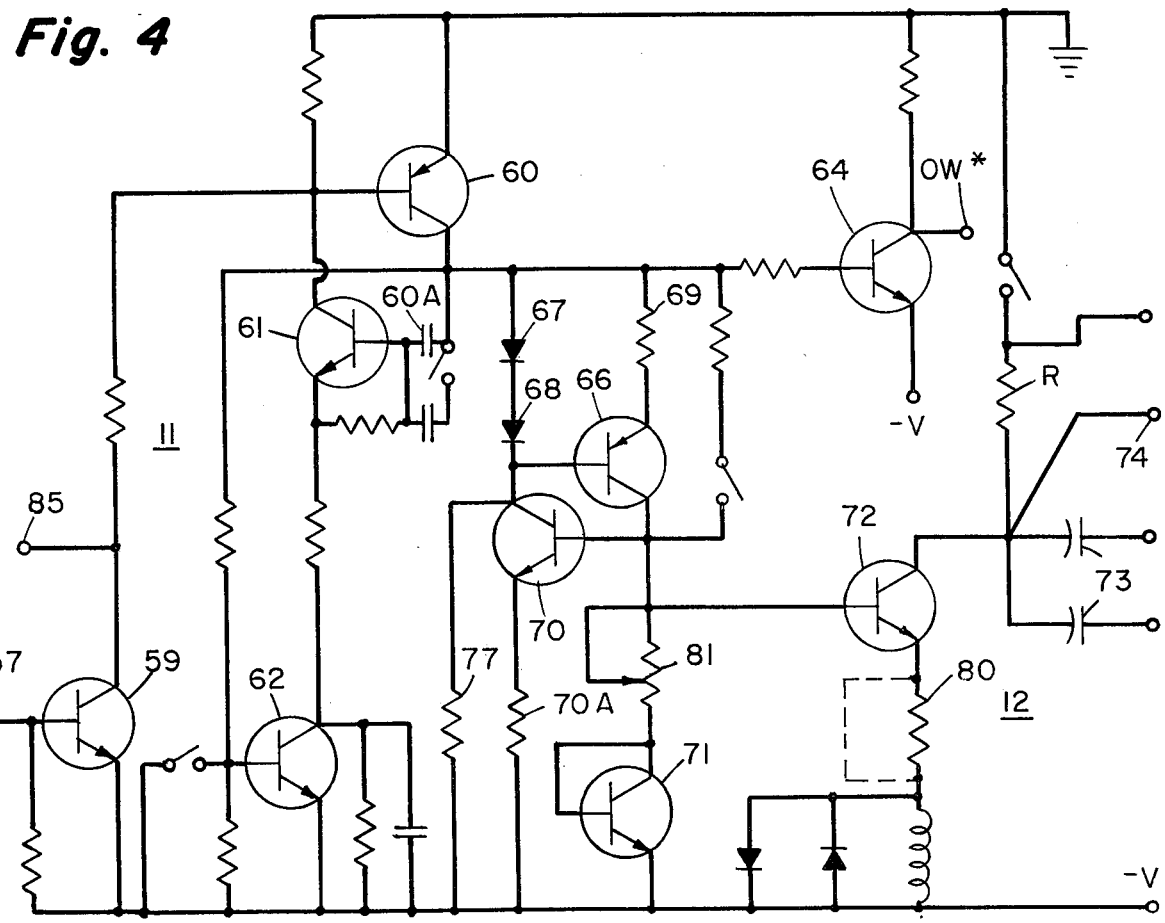

CARDIAC PACER SYSTEM AND METHOD WITH CAPTURE VERIFICATION SIGNAL

BACKGROUND

The present invention relates to cardiac pacers. Many different types of cardiac pacers are known, such as fixed rate pacers and demand or ventricular inhibited pacers. In fixed rate pacers, circuitry generates a train of stimulating pulses of constant period or interval (approximating the interval between natural heartbeats), and these pulses are coupled to the heart to force its rhythm. In a demand type of pacer, the natural activity of the heart is sensed (usually at the ventricle), and this information is used to inhibit the pacer circuitry from generating a pulse. In this type of pacer, it may be said that the electronic circuitry does not "compete" with a natural heartbeat. The interval between the last natural heartbeat to be sensed and the first stimulating pulse is referred to as the "escape interval". It is common practice to have the escape interval in this type of pacer adjusted to a value which will maintain a desired rate of pacing in the absence of naturally-occurring heartbeats.

There are other types of pacers, and there are many variations within each broad classification, such as so-called "hysteresis" pacers which have different escape intervals following sensed or paced beats. For example, the first escape interval may be relatively long, and subsequent escape intervals may be shorter.

Another type of pacer, namely that disclosed in U.S. Pat. No. 3,662,759, granted May 16, 1972, senses a natural heartbeat, and if it occurs, generates a non-stimulating "tracking" pulse in synchronism with a naturally occurring heartbeat. If no natural heartbeat is sensed, then at the end of the escape interval a pulse of greater energy, sufficient to stimulate the heart, is generated. In a non-competing pacer of this type, the tracking pulse may communicate to a physician (over a telephone communication line), that the heart is working in natural sinus rhythm, and that the implanted circuitry is also operational and functioning properly. If, during an examination, the heart is functioning normally and the pacer circuitry quiescent, the tracking pulse assures an examining physician that the circuitry is operative, the power supply functioning, and the electrode system intact (the tracking pulse usually being sensed right at the heart).

Still another type of pacer system is referred to as a threshold tracking pacer. In these systems, the pacing circuitry tries to measure the threshold which is just sufficient to stimulate the heart. It will be appreciated that the stimulating threshold not only varies from person to person, but may vary with time for the same person, and it may change for different electrode systems. Once a stimulating threshold is measured, a system of this type may increase the stimulation by a fixed amount for subsequent pulses, or it may be programmed to seek the threshold anew at fixed times, or each time that natural sinus rhythm is lost. In pacers of this type, it is important to determine when a stimulating pulse is or is not actually stimulating the heart. In this context, "stimulation" means that the pulse transmitted to the heart electrode causes depolarization and contraction of one of the heart chambers, for example, the ventricle. The determination that a stimulating pulse has produced cardiac depolarization or "capture" is referred to as "capture verification". A threshold tracking pacer system is disclosed in an article "Automatic Threshold Tracking Pacemaker", Preston and Bowers, MEDICAL INSTRUMENTATION, Vol. 8, No. 6, November-December, 1974. The article does not disclose the circuitry used, but it describes four separate electrode systems. The first system used four electrodes—two for pacing and two different electrodes for sensing capture. A second electrode system used three electrodes, two of which were positioned in the heart by a catheter, and a third large electrode was remote (perhaps in the abdominal region where artificial pacers are normally implanted). Pacing was from the distal tip electrode to the remote electrode, and sensing was from the second embedded electrode to the remote electrode. The third electrode used a bipolar electrode catheter and a large reference electrode attached to the body surface and, as described, exhibited sensing problems at high current levels. The fourth electrode system used a bipolar catheter with both electrodes used for pacing and sensing. A bipolar catheter is one which has two electrode surfaces, electrically isolated, at the distal end of a catheter. This electrode system, as indicated, produced sensing difficulties due to residual after-potential and electrode polarization. The authors conclude that a three-electrode system is necessary for proper sensing.

Electrode polarization is a well-known phenomenon caused by the interface between the metal surface of the electrode and the ions in solution in the body tissue with which the electrode communicates. In this connection "polarization" refers to a residual voltage resulting from the accumulation of charge at the interface between the electrode metal surface and the electrolyte or body fluid; and it is not to be confused with depolarization of the cells of the heart which accompanies contraction. The polarization voltage may be small, of the order of 0.5–1.7 volts, but it is a significant factor in capture verification because the sensing system is trying to detect the presence of an R wave voltage of the order of 10 millivolts to verify capture, and this signal is small in comparison with normal polarization voltages. In addition to the difference in magnitude between a typical polarization voltage and a stimulated R wave, a polarization voltage does decay with time, and the slope of the decaying voltage even further complicates the detection of a stimulated R wave, as will be further discussed within. Thus, the effect of electrode polarization, in terms of an electrical equivalent circuit, is that it appears to the driving circuitry that the electrode has capacitance which stores some residual charge after stimulation, and reference will be made, then, to an electrode capacitance. The value of the capacitance depends on the material of the electrode and its size.

Another cardiac pacer which senses capture and decreases the amplitude of a succeeding stimulating pulse if a stimulated heartbeat is sensed is disclosed in U.S. Pat. No. 3,757,792, issued Sept. 11, 1973. In this patent, if the circuitry does not sense a stimulated R wave after a stimulating pulse is transmitted to the heart, the next succeeding stimulating pulse is increased in amplitude by a predetermined amount. As stated in the patent, separate pairs of electrodes are used for stimulating and for sensing to avoid the problem of electrode polarization and the resulting refractory period.

The desirability of a single electrode system for both stimulating and sensing capture verification is apparent because of the resulting simplicity in electrode design and operation. However, to our knowledge, workers in the art have been unable to produce an operable, reliable system for indicating capture verification using only a single electrode implanted in the heart for both sensing and detection. The present invention is directed to such a system. The second electrode is remotely located—for example, in the abdomen where the circuitry is normally implanted.

SUMMARY OF THE INVENTION

The present invention may be used in many different types of cardiac pacers, such as demand pacers or fixed rate pacers. For simplicity, the present invention is disclosed in a fixed rate pacer. Further, persons skilled in the art will readily appreciate that there are many uses other than automatic threshold tracking described above to which a capture verifying system may be directed. For example, the electrocardiogram of a patient may be sensed and transmitted through telemetry or telephone lines to a physician at his office or to a clinic. If, during such a test the heart is malfunctioning, the information that the pacer is both generating a stimulating pulse and the heart is responding to it would be very important. In connection with EKG telemetry, reference is made to Lewyn, "An Implantable Multichannel Biotelemetry System", PROCEEDINGS IEEE INTERCON, April, 1975. Such a system of telemetry would be particularly useful in the case where it is desirable to amplify and transmit the shape of the QRS following a stimulating pulse. If it is not desired to transmit the shape of the QRS but rather a single pulse which indicates that an R wave was present, then the invention can be used in conjunction with a pacer which also provides a tracking pulse, as described in the above-identified Dabolt patent, which tracking pulse is presently used to indicate that the heart is functioning normally, and the pacer circuitry is operational, but dormant so as not to compete with the heart. Other applications will be apparent to persons skilled in the art, as indicated.

Briefly, according to the present invention, a cardiac pacer system includes an oscillator for establishing the pacing interval and a driver circuit responsive to the output of the oscillator for generating a stimulating signal which is capacitor-coupled to a single electrode engaging the heart.

A sense amplifier operating in a differential mode has its signal input coupled to the heart electrode for sensing an R wave. In particular, the signal input of the sense amplifier is connected to the circuit or "input" side (as distinguished from the heart or "output" side) of the output coupling capacitor by means of a controlled semiconductor switch.

There are a number of electronic switches in the present system for performing the various functions required, and to avoid confusion, each of the principal switches is referred to by a capital letter. The switch just mentioned is referred to as switch D.

Another switch, switch F, is connected in series with the discharging resistor R for the output coupling capacitor. A third switch, switch A, is used to connect the circuit side of the output coupling capacitor to a clamp potential (which in the illustrated embodiment is ground) through a resistor 17.

A fourth switch, switch E, is used to selectively change the gain of the sense amplifier. Finally, there are two switches, referred to as switches B and C, which are used to connect the signal and reference inputs of the differential sense amplifier in common and to a single reference voltage. The functions of these switches, and the timing of operations will be discussed in more detail within. However, briefly, when a stimulating pulse is generated, as signaled by the oscillator circuit, switch F is immediately switched to a non-conducting state to de-couple the discharging resistor from the output coupling capacitor. This resistor is not reconnected until the period has passed during which a stimulated R wave signal is expected. One of the principal reasons for disconnecting the discharging resistor is to eliminate the current which would otherwise flow to discharge the output coupling capacitor and therefore give rise to a time rate of charge of voltage during the time when the sense amplifier is trying to verify capture by sensing a stimulated R wave.

At the same time, that is at the initiation of a stimulating pulse, the signal input to the sense amplifier is uncoupled from the electrode by switch D; and the sense amplifier is restrained by connecting both its signal and reference inputs in common to the reference voltage source via switches B and C. Further, the gain of the amplifier is reduced because the minimum R wave signal response of the heart to an artificial stimulating signal is usually greater than the minimum value of a natural R wave.

When the stimulating pulse terminates, the discharging of the electrode capacitance is initiated by closing the clamp resistor circuit through switch A. The value of the clamp resistor and the clamp time are such as to remove a certain amount of charge from the electrode capacitance. During clamping, the charge on the output coupling capacitor assists in discharging the electrode capacitance, because during clamping, the output coupling capacitor is connected across the electrode capacitance with an opposite polarity charge so that charge stored on the output coupling capacitor is used to directly discharge the electrode capacitance. This has the effect of greatly reducing, but not entirely eliminating, charge on the electrode capacitance. The electrode is discharged to a level where the voltage slew rate is negligible. There also remains some residual voltage at the output coupling capacitor.

After the clamp is terminated, but before amplifier restraint is removed (inputs still tied in common), the amplifier is reconnected to the output coupling capacitor. At this time both input terminals of the amplifier are connected to a reference voltage. Thus, the amplifier input coupling capacitor is quickly charged to offset the residual voltage on the circuit side of the output coupling capacitor while the amplifier inputs are clamped to the reference voltage. This prevents overdriving the sense amplifier during the time it is being reconnected to the output coupling capacitor. Further, by establishing the offset voltage on the amplifier input coupling capacitor to compensate for residual voltage on the output coupling capacitor, the amplifier does not see a voltage step (which would also overdrive it) when amplifier restraint is removed.

Thus, the amplifier inputs are at the same potential, and the voltage slew rate at the output coupling capacitor is almost zero in a very short period (about 18 Msec.) after a stimulating pulse and prior to the sensing period for verifying capture. During the sensing period, the switches B and C are open. After the sensing period, the (discharging) resistor R for the coupling capacitor is reconnected, and the gain of the sense amplifier is increased to its initial value.

An important aspect of the present invention is that we have discovered that the effect of polarization voltage for materials normally used as heart electrodes can be compensated in a sufficiently short time—typically within 18 milliseconds of the initiation of a stimulating pulse—to permit detection of stimulated R waves. The sense amplifier is selectively coupled to the heart electrode at a time when the signal at the heart electrode is quiescent at least to the extent that a stimulated R wave can be detected when it is expected. Further, the clamping, compensation and sensing technique employed by the present invention is adaptable to different types of electrode materials. This is significant because each type of material exhibits its own characteristic polarization voltage and electrode capacitance.

Another important aspect of the present invention is that it provides a means for removing energy from an electrode, immediately following stimulating, without requiring additional energy from the power source. That is, the electrode energy is removed by passive circuit means (the clamp resistor and output coupling capacitor), and it is effective over a wide range of input currents.

Another important aspect of the present invention is the driver circuit which provides a constant output current for stimulation, and the value of the output current remains constant and is independent of the magnitude of the source voltage over a wide range—down to near failure. This is particularly important in an implanted stimulating device such as a cardiac pacer where it is desirable to maintain a constant output current even under conditions of diminished supply voltage.

Still another important aspect of the present invention is that it provides a capture verification signal for a cardiac pacer using only a single electrode contacting the heart—that is, the same electrode is used for both stimulation and for sensing. This is useful in various types of cardiac pacers, including both fixed rate pacers and non-competing or demand pacers.

As mentioned, the signal input of the sense amplifier is disconnected from the heart electrode, in a single electrode system, during the time that the stimulating pulse is present on the electrode. This, in conjunction with the amplifier restraint, gain reduction and basic amplifier configuration advantageously prevents overloading the sense amplifier. Further, by reducing the gain of the amplifier during the time that a stimulated R wave is being sensed, the same circuitry may be used for sensing both stimulated and naturally occurring R waves; and this may be useful both in fixed rate and demand pacers.

As will be clear from the detailed description following, amplifier restraint begins at the initiation of a stimulated pulse, and it extends until a time beyond which the amplifier is reconnected to the electrode. Thus, the amplifier is not operative to sense capture until sometime beyond which all the switching is performed for electrode compensation, and the amplifier therefore is not responsive to the switching noise. Further, the amplifier is initialized in a manner such that it is not overloaded by the offset voltage present at the circuit side of the output coupling capacitor when the amplifier is reconnected for sensing.

Other features and advantages will be apparent to persons skilled in the art from the following detailed description of one embodiment, accompanied by the attached drawing.

THE DRAWING

FIG. 1 is a circuit schematic diagram, partly in functional block form, of a cardiac pacer system with a capture verification signal, incorporating the present invention;

FIG. 3 is a circuit schematic diagram of the oscillator circuit of FIG. 1;

FIG. 4 is a circuit schematic diagram of a monostable and constant current drive circuit of FIG. 1;

FIG. 5 is a circuit schematic diagram of a circuit for generating the SRWI signal;

FIG. 6 is a schematic diagram of a circuit generating the IWEN signal; and

DETAILED DESCRIPTION

Figure 2:
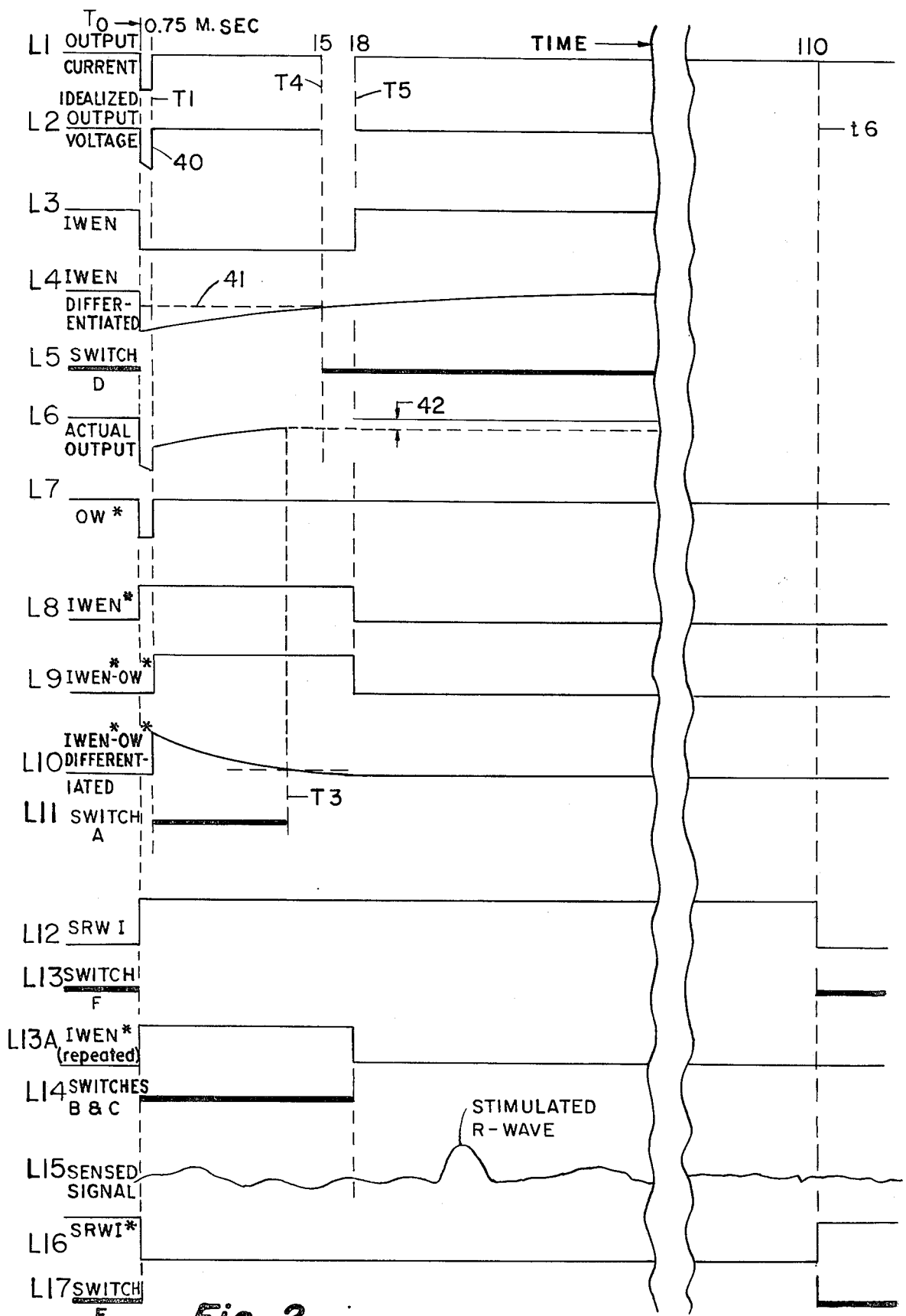
FIG. 2 is a timing diagram showing various voltages and relative switching times in the circuitry of FIG. 1.

Referring now to FIG. 1, reference numeral 10 designates an oscillator circuit for generating a periodic train of pulses. As indicated, the illustrated embodiment is a fixed rate cardiac pacer, and the output pulses of the oscillator circuit may, for example, occur at intervals of 833 milliseconds. These pulses are fed to a monostable circuit 11 which converts each pulse in the output train to a corresponding pulse of fixed time duration or width (0.75 Msec.). The output of the monostable circuit 11 is coupled to a constant current driver 12, the output of which is connected to an output coupling capacitor C1. The other terminal of the output coupling capacitor C1 is connected to the heart electrode, diagrammatically represented by the dashed block 14. The simplified electrical equivalent circuit of the heart electrode 14, due to polarization effect, as discussed above, is a capacitance as diagrammatically shown in dashed line and designated C2. The circuit is completed through the body tissue to a remotely located common electrode. The resistance of the heart and body tissue is shown as a dashed resistor designated $R_H$.

As viewed in FIG. 1, the left side of capacitor C1 is sometimes referred to as the "circuit side" because the pacer circuitry is connected to it, and for analogous reasons, the right side is sometimes referred to as the "heart side". The circuit side of the output coupling capacitor C1 is connected to a series circuit comprising a discharging resistor R and a switching transistor F, the emitter of which is grounded. The base terminal of the switch F is connected to the output of an SRWI signal generator represented by the block 16, which receives its input signal from the output of oscillator circuit 10. Briefly, the SRWI signal generator 16 generates a signal having an interval which defines a time from the beginning of a stimulating pulse until the end of the period in which a stimulated R wave is expected to occur. Hence, this signal is sometimes referred to as the Stimulated R-Wave Interval (SRWI) signal. The signal is shown on line L12 of FIG. 2, and the state of switch F is correspondingly shown on line L13. In this line diagram, a switch in a conducting state is represented by a heavy line, and the absence of such heavy line indicates those times during which the corresponding switch is in a non-conducting state. It will thus be observed by way of example, that switch F is non-conducting (line L13) during the time when the SRWI signal (line L12) occurs.

Returning now to FIG. 1, the circuit side of the output coupling capacitor C1 is also connected to a series circuit comprising a CMOS switch A, and a clamping resistor 17. The same junction is similarly connected to a series circuit comprising a CMOS switch D, a capacitor C3 (sometimes referred to as the amplifier input coupling capacitor) and thence to the signal input 18 of amplifier 20, which is sometimes referred to as a "sense" or "output" amplifier. The output of the amplifier 20 is a signal representative of a stimulated or natural R wave.

The amplifier 20 is preferably a differential amplifier, and it includes a reference input terminal 21 which is connected through a capacitor C4 to ground. Signal input terminal 18 of the amplifier 20 is connected via a CMOS switch C to a reference voltage $V_{REF}$; and the reference input terminal 21 is similarly connected by means of a CMOS switch B to $V_{REF}$. The voltage $V_{REF}$ is derived from the power source for the pacer unit, and is diagrammatically illustrated by a voltage source 23, and a capacitor 24 connected in parallel with the source 23.

A CMOS switch E is connected in the feedback circuit of amplifier 20. This is a schematic representation for the fact, to be discussed more fully below, that when switch E is conducting, the gain of the sense amplifier 20 is decreased by a predetermined amount. In one embodiment, the gain of the amplifier 20 is reduced by a factor of four when the switch E is conducting. The amount by which the gain is decreased depends upon the anticipated differences in magnitude between the minimum value expected for a stimulated R wave and a naturally occurring R wave. The switch E is energized by the complement of the SRWI signal (denoted SRWI*) which is received from inverter 16A. As indicated, it is during this time that the heart electrode is monitored for detection of capture by a stimulating signal.

The output of the oscillator circuit 10 is connected to the input of a circuit 27 which generates a signal called IWEN. This signal is sometimes referred to as the Input Wave Enable IWEN signal. The output of the IWEN generator 27 (line L3 of FIG. 2) is connected to a differentiator circuit 28 (see line L4 of FIG. 2) and to an inverter circuit 29. The differentiator circuit 28 feeds the gate lead of the previously discussed switch D.

The output of the inverter circuit 29 is the IWEN* signal (the complement of a signal again being indicated by an asterisk) (line L8 of FIG. 2); and it is coupled to the gate terminals of switches B and C, and to the input of a gate circuit 30. The IWEN* signal defines a short period of time following a stimulating signal (18 Msec. in the illustrated embodiment) and prior to the period when the circuit is to determine whether the stimulating signal has actually stimulated or "captured" the heart, within which the electrode capacitance is compensated. The gate circuit 30 is shown as having an inhibit input I, which is received from a circuit 32 which generates a signal called OW*, which is derived from the output of the monostable circuit 11. Briefly, the OW* signal inhibits the transmission of the IWEN* signal through the gate 30 for a period of time equal to the time duration or width of the stimulating pulse, as will be further discussed below. The OW* signal is shown on line L7 of FIG. 2, and the output signal of the gate 30 is shown on line L9. The output signal of gate 30 is fed to a differentiator circuit enclosed within the dashed block 33; and it includes a resistor 34, a switch 35, having two positions A and B, and first and second capacitors 36, 37. Depending upon the position of the switch 35, one of the capacitors 36, 37 will be connected in series with the resistor 34. The capacitors 36, 37 are selected so as to provide different time constants, depending upon the electrode material, and more particularly, upon the electrode capacitance, as will be made clear below. The differentiated output signal of gate 30 is connected to the gate lead of switch A.

System Operation

Referring to FIGS. 1 and 2, the output of the oscillator circuit 10 is connected to trigger the monostable circuit 11 at $T_0$ which generates an output pulse having a duration of 0.75 Msec. This signal is then fed to the current driver 12 which generates a negative-going output current pulse, shown on line L1 of FIG. 2, having a constant magnitude and fixed duration of 0.75 Msec. This is the pulse that is transmitted through the output coupling capacitor C1 to the heart electrode for stimulation; hence it is sometimes referred to as a stimulating pulse. If the heart is stimulated, a corresponding signal (called a stimulated heart signal) will be sensed in the period 18–110 Msec. of the initiation of each cycle. The corresponding voltage at the circuit side of the output coupling capacitor is shown in idealized form on line L2 of FIG. 2 as pulse 40. The actual output voltage includes the effects of electrode capacitance, and, hence, it looks more like the waveform shown on line L6, as will be further explained.

Referring now to line L3 of FIG. 2, the output signal of the IWEN generator 27 is shown as a signal having a duration of 18 milliseconds, terminating at time T5 in the timing diagram. This signal is differentiated in differentiator circuit 28, the output of which is coupled to switch D. The differentiated IWEN signal is shown in line L4, and when it goes negative, switch D becomes non-conducting (see line L5) to thereby isolate the signal input 18 of the amplifier 20 from the output of the current driver 12. When the differentiated IWEN signal rises to a predetermined threshold level indicated by the line 41, and determined by the threshold voltage of the switch D, the switch D will again become conducting, as indicated at time T4 in FIG. 2. It will be apparent that time T4 (which may be about 15 milliseconds) is prior to time T5 which marks the end of the IWEN* period. This means that the amplifier restraint is removed only after the signal input 18 of the amplifier 20 is reconnected to the output coupling capacitor C1, as will be more fully explained below.

Referring now to line L6 of FIG. 2, there is shown a more realistic voltage waveform as might exist on the circuit side of the output capacitor C1 for a given electrode material. The curve is characterized by an initial negative-going step, a less negative-sloped portion (during the stimulating current pulse) which is caused by electrode polarization, followed by a positive-going step when the stimulating pulse terminates, then a decaying positive portion caused by discharging of the output coupling capacitor, and finally a residual level indicated by a dashed line when the clamp is removed.

The IWEN generator 27 is a monostable circuit which generates a pulse of duration of 18 milliseconds as shown on line L3 of FIG. 2 and previously explained. This pulse is inverted in the inverter circuit 29, the output pulse of which is shown on line L8 of FIG. 2. The OW* signal generator is responsive to the output of the monostable circuit 11 to generate a pulse having a width equal to the width of the stimulating pulse, as shown in line L7 of FIG. 2. This signal is used to inhibit the transmission of the IWEN* signal through gate 30. Hence, the resulting signal [IWEN* ·OW*] is shown on line L9 as extending from the period 0.75 milliseconds to 18 milliseconds. This pulse is differentiated in the differentiator circuit 33, as shown in line L10 with the switch 35 in the A position (capacitor 36 connected in circuit). The output of the differentiator circuit 33 causes the switch A to conduct, thereby clamping the circuit side of the output coupling capacitor C1 to ground through the clamping resistor 17. The value of the clamping resistor 17 is small compared with the value of the discharging resistor R, and it thereby rapidly discharges the output coupling capacitor C1. Further, by clamping the circuit side of the output coupling capacitor C1 to ground, this capacitor is now discharged in parallel with the electrode capacitor C2, with the polarities of stored charges opposing, whereas during stimulating, they had been charged in series. In other words, during stimulation, the charges on the capacitor C1, C2 are cumulative, whereas during clamping, they are opposing so that some of the charge on capacitor C1 is used to discharge the electrode capacitor C2. Thus, the output coupling capacitor is rapidly discharged, and some of the charge on the output coupling capacitor is used to discharge the electrode capacitance. Compensation for the electrode capacitance is thus effected by passive circuit means, and it is considered an important aspect of the present invention that the discharge of the output cooling capacitor and electrode compensation be accomplished within a time period prior to that during which a stimulated heart signal is expected to occur because during this time, the signal input of the amplifier 20 is disconnected and, therefore, not able to sense the R wave. The time during which the output coupling capacitor C1 is clamped to ground (determined by the differentiator circuit 33) and the value of the clamping resistor 17 are related to the various parameters, such as the electrode material (which determines electrode capacitance), and the value of the output coupling capacitor so as to achieve this discharge in the required time. It is considered an advantage of the invention that proper compensation can be achieved by this method for a wide range of stimulation current levels. As indicated on line L6, after the clamp is removed, and during the time period for verifying capture (18 milliseconds to 110 milliseconds) as indicated by the dashed portion, there is a residual charge resulting in voltage level 42, but the rate of change of voltage is very small compared to the rate of change of voltage that would otherwise occur if there were no clamping. The slight offset voltage 42 is a function of system parameters; and it is accounted for when the amplifier is reconnected.

The output of the IWEN generator 27 is also fed to a second differentiator circuit 28, the output of which is connected to the gate of switch D. The time constant of the differentiator circuit 28 is longer than the longest time constant for the differentiator 33, but less than the duration of the IWEN signal so that the signal input 18 of the amplifier 20 may be disconnected during stimulation and clamping, but reconnected to the heart electrode prior to removal of amplifier restraint, to be discussed presently. This is illustrated in lines L4 and L5 which show respectively the differentiated IWEN* signal when diminishes until it reaches the previously described threshold 41, during which time the switch D is in a non-conducting state.

Referring now to lines L12 and L13 of FIG. 2, the SRWI signal causes switch F to become non-conducting from the beginning of a stimulating pulse until the time period for capture verification has ended, after which time switch F becomes conducting to enable the output coupling capacitor C1 to completely discharge. The SRWI* signal, as mentioned, is fed to switch E to change the gain of the amplifier 20; see lines L16 and L17 of FIG. 2.

Turning now to the circuitry which restrains the amplifier 20, the IWEN* signal is repeated beneath line L13 as line L13A of FIG. 2. This signal also causes switches B and C to conduct from a time beginning with the initiation of a stimulating pulse until the beginning of the actual sensing period (18 milliseconds after the initiation of a stimulating pulse).

When switches B and C are conducting, the signal input 18 and reference input 21 of the amplifier 20 are connected together. Thus, insofar as any signal at the heart electrode is concerned, the amplifier is changed from a differential mode of operation to a common mode of operation. Because amplification is much greater in the differential mode of amplification (gain of the amplifier being unity in the common mode), signals of large magnitude during this period do not overdrive the amplifier. Further, the signal input 18 and the reference input 21 of the amplifier 20 are connected to a reference voltage $V_{REF}$. This voltage provides a reference to which the residual voltage on the output coupling capacitor is restored after the clamp is removed (see voltage 42 on line L6 of FIG. 2). The residual voltage must be prevented from appearing an a signal at the amplifier 20 because this would overload the amplifier. The amount of residual voltage depends upon the electrode material, and referring to line L6, it may be relatively small for a platinum electrode or it may be relatively large for an Elgiloy electrode, the two most commonly used materials. Both amplifier inputs 18 and 19 are directly connected to $V_{REF}$ (switches B and C are closed) at the time the amplifier is reconnected to the output coupling capacitor (switch D becomes conducting). Thus, when switch D conducts, the amplifier input coupling C3 charges to a voltage necessary to offset any residual voltage on the output coupling capacitor C1, and the amplifier is prevented from responding to any such residual voltage.

To summarize the operation and timing of compensation using a single electrode, immediately after the stimulating pulse terminates, switch A conducts to clamp the circuit side of the output coupling capacitor C1 through the resistor 17 to ground. At the same time, capacitor C1 has a charge which has an opposing polarity to the charge on the electrode capacitance C2 during clamping. Thus, the charge on capacitor C1 is used to partially discharge or neutralize the charge on the electrode capacitance during clamping.

Clamping ends at time T3 in FIG. 2—well before the end of the IWEN* period and before, it will be observed, the amplifier is reconnected when switch D closes at time T4. Between time T4 and the end of the IWEN period, time T5, the amplifier input coupling capacitor C3 is charged to a voltage sufficient to offset any residual voltage on the output coupling capacitor C1, such as that represented by the offset voltage 42 on line L6 of FIG. 2. This occurs while the amplifier inputs are connected in a common mode and they are both connected to the reference voltage source. Hence, the amplifier does not "see" or respond to any of the abrupt voltage changes that may be occurring due to the switching of switches A and D. Finally, after the input coupling capacitor C3 is sufficiently charged to offset any residual voltage on the output coupling capacitor C1, amplifier restraint is removed by causing switches B and C to become non-conducting. All of this occurs within 18 milliseconds of initiation of a stimulating pulse, and prior to the time during which a stimulated heart signal is detected, which would verify capture.

Individual Circuits

Referring now to FIG. 3, there is shown a conventional oscillator circuit including transistors 50 and 51 connected in cascade, the base of transistor 50 being connected to the collector of a transistor 51. Capacitors 53, 54 are connected between ground and the emitter of transistor 51, and an RC time constant is determined by the value of the capacitance and the combined resistance of a fixed resistor 55 to a variable resistor 56. In operation, when the transistors 50, 51 conduct, they discharge the capacitors so that the output voltage goes toward ground. A very fast leading edge is produced by the regenerative effect caused by transistors 50, 51. After the capacitors have discharged, the transistors 50, 51 become non-conducting, and the output signal goes negative as determined by the RC time constant. The repetition rate of the pulses may be varied by adjusting the resistor 56. Transistor 50A is connected as a diode, and together with its associated biasing resistors acts to keep the base of transistor 51 at a constant voltage. Transistor 52 is used as a means of turning off the oscillator after it has been reset, if desired, so that during the reset cycle, if transistor 52 is caused to conduct, the base of emitter 50 is clamped to the negative supply, and the oscillator will reset.

Turning now to FIG. 4, a circuit schematic is shown for the monostable circuit 11 and current driver 12. The monostable circuit 11 acts as a buffer amplifier for the output signal taken from node 57 of the oscillator circuit of FIG. 3, and it includes transistors 59, 60, 61 and 62. The output of transistor 59 is coupled to the cascaded transistors 60, 61, and the output signal is taken from the junction between the collector of transistor 60 and a coupling capacitor 60A connected to the base of transistor 61. This monostable circuit is also of conventional design. When transistor 60 conducts, a voltage is fed through capacitor 60A to turn on transistor 61. When base current stops flowing through transistor 61 (the capacitor discharges) the circuit turns off. The output signal of the monostable circuit 11 is connected to the base of a transistor 64. The signal OW* is taken from the collector of transistor 54.

The remaining circuitry of FIG. 4 forms the constant current driver 12, and this circuit is considered to be very advantageous in use because the output signal remains constant in current over a very wide range of source voltages and it represents an improvement over previous designs in this respect. It will be appreciated that this characteristic is especially important in an implanted cardiac pacer. Further, as is also desirable in a cardiac pacer, the circuit has the characteristic of a low output saturation voltage even though the output voltage swing is very nearly equal to the voltage of the power source. This permits better use of the available voltage.

The driver circuit includes a first transistor 66 which is connected in series with diodes 67, 68 and a resistor 69 in a conventional manner to form a constant current source. The diodes 67, 68 are forward biased, and the emitter-base junction of transistor 66 is also forward biased. Hence, the voltage across resistor 69 is constant, and the collector current remains constant. The base current is kept constant by a first current mirror comprising a transistor 70, resistor 70A, and a transistor 71. Transistor 71 is used as a common diode in a second current mirror which includes transistor 72. The output of the circuit is taken from the collector of transistor 72, the capacitors 73 forming the output coupling capacitor to the heart electrode. The terminal 74 is connected directly to switches A and D, as disclosed above. The collector of transistor 72 is also connected through a resistor 75 to the input of the SRWI generator (FIG. 5, to be discussed).

In operation, the current mirror formed by the transistor 70 and diode 71 act as a feedback circuit to establish a constant current in the diodes 67, 68. A resistor 77 is present from the base of transistor 66 to the negative supply, but it has a large value, and even with its presence, as indicated, the feedback current mirror acts to stabilize the operating current of the constant current source. The current gain in the feedback loop consisting of transistors 69 and 70 is less than one to insure stability. With this circuit, namely, by using a current mirror to establish a constant current in the diodes 67, 68 in the base circuit of transistor 66, the operating voltage of the diodes is rendered substantially independent of fluctuation in the supply voltage. With a constant voltage established at the base of the transistor 66, a constant voltage is established across the resistor 69, and the output current is substantially independent of supply voltage.

The second current mirror, including transistor 72, forms a trans-conductance amplifier with a gain of approximately twenty since resistor 80 (which may be omitted for even higher gain) is much smaller than resistor 70A. This current mirror is driven by the constant current source just described. A variable resistor 81 is included in circuit with the transistor 71, and it is adjustable for adjusting the level of output current. With the output current adjusted on the order of six milliamps, the transistor 72 is capable of delivering a voltage in excess of 5.32 volts from a 5.52 volt battery system. This represents a voltage efficiency of 96.37 percent. Thus, the output voltage capable of being delivered by this system is within 0.2 volts of the terminal voltage, whereas existing circuits can deliver a voltage up to approximately 0.6 volts less than the supply voltage.

Turning now to FIG. 5, the SRWI signal generator is a conventional monostable circuit including transistors 87, 88 which receives its input from the output terminal 85 of FIG. 4. The signal generated at the collector of transistor 88 is the SRWI signal, and it is this signal, as indicated previously, that is fed to the base of transistor F, which is also seen in FIG. 5. The collector of transistor F, as indicated, is connected to the charging resistor R of FIG. 1. The monostable circuit, as indicated, generates a positive-going pulse of a duration of 110 milliseconds which is used to disconnect the charging resistor R (by causing switch F to become non-conducting) and to change the gain of the amplifier 20 (by causing switch E to open via inverter 16A).

Figure 7:
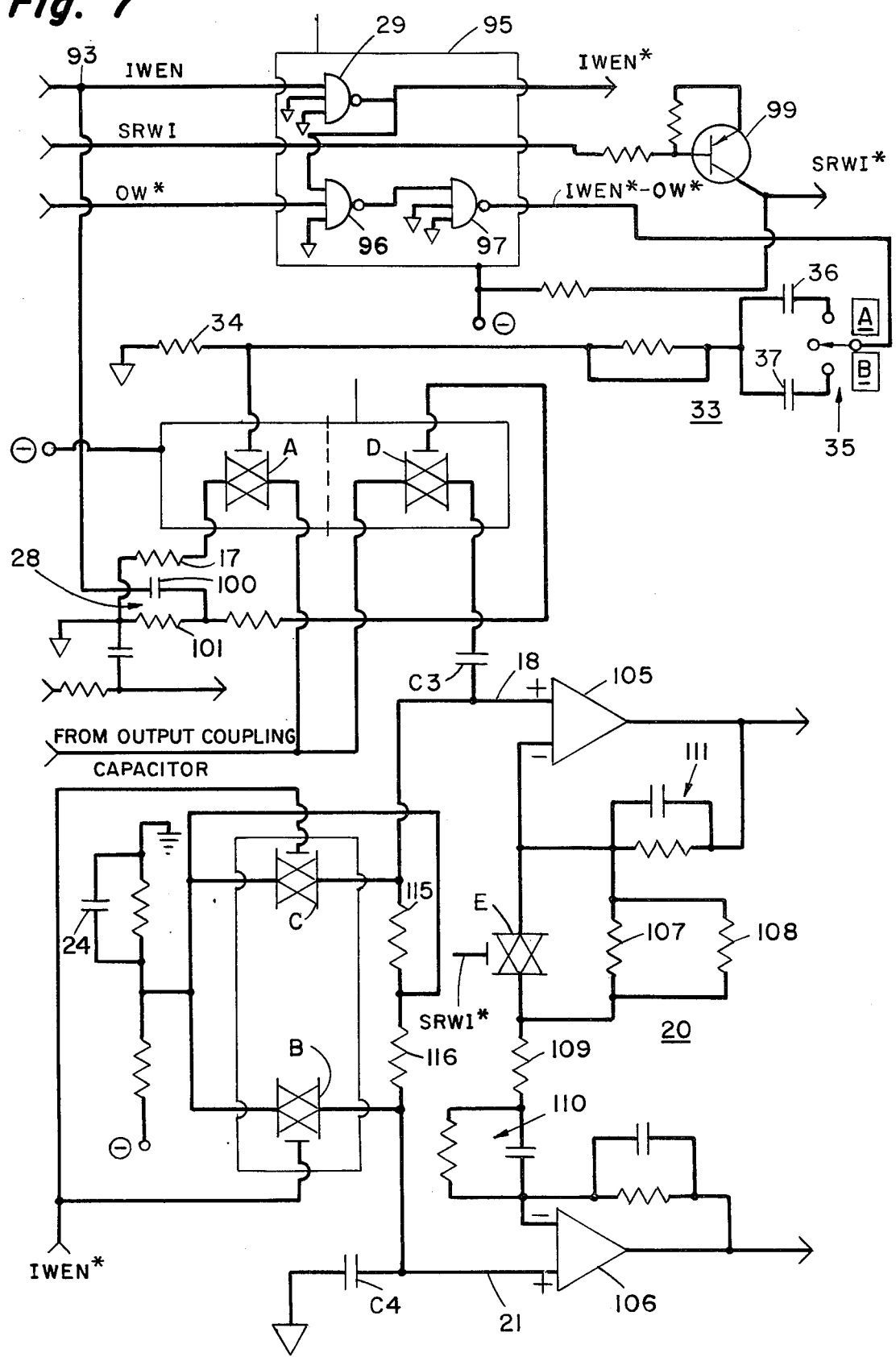
FIG. 7 is a schematic diagram of the control circuitry and the amplifier circuit of FIG. 1.

Turning now to FIG. 6, there is shown a monostable circuit for generating the IWEN signal. The circuit includes transistors 90, 91 which form the monostable circuit; and a transistor 92 which provides a buffer amplifier. The IWEN signal is taken from the collector of transistor 92. The monostable circuit generates a pulse having a duration of 18 milliseconds which is determined by the time constant of the resistor 93 and capacitor 94. The collector of transistor 92 is connected via terminal 93 to the inverter circuit 29 (FIGS. 1 and 7). In FIG. 7, the inverter 29 is shown as a NAND gate connected as an inverter because it is an element of an integrated circuit 95. That is, the integrated circuit includes two additional NAND gates 96 and 97. The output of the inverter 29 is the IWEN* signal, and it is coupled to one input of the NAND gate 96 and to the gate terminals of CMOS switches B and C (see the lower left-hand corner of FIG. 7), which have already been described.

The SRWI signal is coupled to the base of a transistor 99 which acts as an inverter, and the signal SRWI* is taken from the collector of the transistor 99, and fed to the gate lead of switch E (see the lower central portion of FIG. 7).

The OW* signal is fed to the second input of the NAND gate 96, and the output of gate 96 is coupled to an input of NAND gate 97, which is connected as an inverter circuit. Hence, the output signal of NAND gate 97 is the signal IWEN*.OW*. Thus, the NAND gates 96, 97 of FIG. 7 provide the gate 30 of FIG. 1; and the output signal thereof is coupled to the wiper arm of the switch 35, and thence to the differentiator 33, described above. The output of differentiator 33, as indicated, is connected to the gate of switch A, the operation and function of which has already been described.

Still referring to FIG. 7, the IWEN signal is also connected to a capacitor 100 and a resistor 101 which forms the differentiator circuit 28 of FIG. 1. The output signal of the differentiator circuit 21 is connected to the gate lead of switch D, which disconnects the amplifier 20 from the output coupling capacitor, as shown. In a preferred embodiment, the amplifier 20 comprises two instrumentation-type differential amplifiers 105 and 106. The positive input of amplifier 105 comprises the signal input 18, and the positive input of amplifier 106 comprises the reference input 21, the capacitors C3 and C4 being as shown in FIG. 7. Connected between the negative input terminals of amplifiers 105, 106 is the switch E, which, when conducting, shorts out resistors 107, 108 to increase the gain of the amplifier.

The positive input of amplifier 105 is connected to the switch C, as shown, and to a resistor 115. Similarly, the positive input of amplifier 106 is connected to the switch B, and to a resistor 116. The switches B and C short out the resistors 116, 115, when they are in a conducting state, to change the operation of the amplifier from the normal differential mode to a common mode, as explained above.

As mentioned, the gain of the amplifier is determined by the values of resistors 107, 108 and 109 when switch E is non-conducting. When a stimulating pulse has been transmitted to the heart, the gain of the amplifier is reduced by opening switch E and no longer shorting out resistors 107, 108. The values of these various resistors will be determined by the extent to which it is desired to reduce gain during sensing of the stimulated R wave.

Connected between the negative terminals of the amplifiers 105, 106 is a differentiator 110. The function of the differentiator circuit 110 is also important in enhancing the noise immunity of the sense amplifier. Referring to FIG. 2, and particularly, to line L6, after switch A has opened, the voltage at the coupling capacitor will drift slightly negatively, as illustrated by the dashed line. This negative drift is offset by the differentiator 110 which causes a slight offset in the reference voltages in the amplifiers 106 and 107 in a direction opposite to the drift exhibited in line L6.

To summarize the timing of the operation of the amplifier 20, there is a first period (0–18 Msec.) when the input to the amplifier is disconnected from the output coupling capacitor. Following this period (18 Msec.-110 Msec.), the amplifier is connected to sense a stimulated heart signal, but its gain is reduced. This has been referred to as the period during which a stimulated heart signal is expected to occur.

Having thus described in detail one embodiment of the invention, persons skilled in the art will be able to modify certain parts of the system which have been illustrated and to substitute equivalent circuitry for that disclosed while continuing to practice the principle of the invention; and it is, therefore, intended that all such modifications and substitutions be covered as they are embraced within the spirit and scope of the appended claims.

We claim:

1. In a cardiac pacer system including a stimulating electrode contacting a person's heart, said electrode exhibiting capacitance; stimulating circuit means for generating electrical pulses of a first interval for stimulating the heart; and an output coupling capacitor for coupling said pulses to the heart; improved capture verification circuit means for detecting whether the heart has responded to a stimulating pulse comprising: amplifier means adapted to be coupled to said electrode through said output coupling capacitor for sensing a stimulated heart signal and generating a signal in response thereto; clamping circuit means including timing circuit means and first switching circuit means for connecting said output coupling capacitor to said clamping circuit means for a predetermined second time interval after said stimulating pulse has terminated and before said stimulated heart signal is to be sensed; and second switching circuit means for disconnecting said amplifier means from said coupling capacitor when said stimulating pulse is generated and for reconnecting said amplifier means to said coupling capacitor after said predetermined second time interval and before a time period during which said stimulated heart signal is expected to be sensed.

2. The apparatus of claim 1 further comprising an input coupling capacitor connected between one terminal of said output coupling capacitor and a signal input of said amplifier; and wherein said amplifier means comprises a differential amplifier with a signal input and a reference input, said signal input thereof being adapted to be connected to said input coupling capacitor by said second switching means; said system further comprising a reference voltage source; and third and fourth switching circuit means for connecting respectively said signal input and said reference input of said differential maplifier in common and to said reference voltage source for a third predetermined period of time starting when said stimulating pulse is generated and terminating after said second switching means has reconnected said amplifier means to said output coupling capacitor, whereby said differential amplifier is restrained during the period of said stimulating pulse and said second predetermined time interval.

3. The system of claim 1 wherein said system and heart have a common return and said clamping circuit means comprises a passive circuit including a resistor adapted to be connected between said output coupling capacitor and said common return for a clamping time, said clamping time and said resistor being of known value sufficient to remove charge from said output coupling capacitor, and wherein at least some of the charge remaining on said coupling capacitor after stimulating is used to discharge said electrode capacitor during clamping, the rate of change of voltage caused by said discharging being substantially zero at a predetermined time following the end of said clamping.

4. The apparatus of claim 3 wherein said system further comprises a charging resistor for supplying a path for charging said output coupling capacitor after stimulation, said system further comprising fifth switching means for disconnecting said charging resistor during the period in which a stimulated heart signal is expected to occur.

5. The apparatus of claim 3 further comprising compensation charge means for compensating for direct voltage offset at said coupling capacitor when said amplifier means is reconnected to said coupling capacitor.

6. The apparatus of claim 1 wherein said coupling capacitor has stored charge at the end of a stimulating pulse, at least some of said stored charge acting to neutralize the charge stored on said electrode capacitor when said coupling capacitor is clamped during a clamping time, said clamping circuit including a resistor, the value of said clamping resistor and said clamping time being a function of the electrode capacitance and capable of removing substantially all stored charge from said electrode capacitor.

7. In a cardiac pacer system including means for generating electrical pulses at predetermined intervals for stimulating the heart, an electrode for contacting the heart for sensing heart signals, amplifier means coupled to said electrode for detecting stimulated heart signals, output coupling capacitor means interposed between said electrode and said amplifier, and charging resistor means for charging said output capacitor between stimulated heart signals, improved capture verification circuit means comprising: first switching circuit means for disconnecting said charging resistor during a period of time in which a stimulated heart signal is expected to occur; resistive discharge circuit means; second switching circuit means for establishing a discharge path for said coupling capacitor through said resistive discharge circuit means during a period during which a stimulated heart signal is expected to be sensed, at least some of the stored charge on said coupling capacitor compensating the stored charge on said electrode capacitance; and third switching circuit means for selectively connecting said amplifier to said coupling capacitor during said period when a stimulated heart signal is expected to be sensed; whereby said amplifier will generate an output signal responsive to a stimulated heart signal.

8. The apparatus of claim 7 wherein said means for generating said stimulating pulse comprising a constant current driver circuit.

9. A method of verifying that a stimulating pulse of predetermined time duration transmitted from an artificial cardiac pacer to a single heart-engaging electrode through an output coupling capacitor has produced a stimulated R wave wherein a charging means is employed to provide a path for recharging the coupling capacitor after a stimulating pulse comprising:
  selectively disconnecting said charging means in response to a stimulating pulse prior to a time during which a stimulated heart signal is expected to be sensed;
  clamping said coupling capacitor in circuit with the electrode such that the polarity of charge in said coupling capacitor is opposite to the polarity of charge on the electrode capacitance from a time after said stimulating pulse has terminated until a subsequent time before a stimulated heart signal is expected to be sensed to cause at least some of the charge on said coupling capacitor to discharge the electrode capacitance;
  connecting an amplifier to said electrode after said clamping, the output signal of said amplifier being representative of verification of a stimulated heart signal; and
  compensating the signal input to said amplifier for a voltage offset when said amplifier is connected.

10. The method of claim 9 further comprising the step of reducing the gain of said amplifier during the period in which a stimulated heart signal is expected to occur following a stimulating pulse from said artificial cardiac pacer.

11. The method of claim 9 wherein said amplifier is a differential amplifier with an input coupling capacitor and said step of compensating said amplifier comprises disconnecting the signal input lead of said amplifier from said coupling capacitor during the generation of a stimulating pulse and during said clamping period; restraining said amplifier by connecting the signal and reference input terminals of said amplifier to a common reference voltage during a period extending from the generation of a stimulating pulse until a time after said clamping period; reconnecting the amplifier input coupling capacitor to said output coupling capacitor; and then removing the amplifier restraint.

12. In combination with an artificial electronic cardiac pacer for generating periodic stimulating pulses and transmitting said pulses through a coupling capacitor to a single heart-engaging electrode and including a recharging resistor for said coupling capacitor; circuitry for verifying that a stimulating pulse has produced a stimulated R wave comprising:
  amplifier means for sensing a stimulated R wave at said coupling capacitor; first switching circuit means responsive to a stimulating pulse for disconnecting the input of said amplifier from said coupling capacitor from a predetermined time starting with said stimulating pulse until a time prior to a period during which a resulting stimulated R wave is expected to occur; and means coupled to said electrode for compensating for polarization of said electrode during said predetermined time; said first switching means reconnecting said amplifier input to said coupling capacitor after said predetermined time; the output of said amplifier being representative of a stimulated heart signal.

13. The apparatus of claim 12 further comprising circuit means responsive to the generation of a stimulating pulse for reducing the gain of said amplifier means only during the time period in which a stimulated heart signal is expected to occur in response to said stimulating pulse.

14. The apparatus of claim 12 wherein said amplifier means comprises a differential amplifier having a signal input terminal adapted to be connected to said coupling capacitor and a reference input terminal, said system further comprising second switching circuit means for connecting said signal input terminal of said amplifier means to said reference input terminal from a time beginning with the generation of a stimulating heart pulse until a time subsequent to the re-connection of said amplifier to said output coupling capacitor but prior to the period in which a stimulated R wave is expected.

15. The apparatus of claim 14 wherein said means for connecting said amplifier terminals together includes a reference voltage source; means for connecting said terminals to said reference voltage source having a magnitude sufficient to properly bias the amplifier and compensate any dc offset voltage existing at said coupling capacitor when said amplifier is reconnected thereto.

16. The apparatus of claim 14 wherein said differential amplifier means comprises first and second differential amplifiers each having a first polarity input terminal and a second polarity input terminal, the first polarity input terminals of said amplifiers forming respectively said signal input terminal and the reference input terminal of said amplifier means, said system further comprising differentiator circuit means connected between the second polarity input terminals of said amplifier means for compensating for any offset in the voltage level at said coupling capacitor after said clamping has terminated.

* * * * *